United States Patent [19]

Shturman et al.

[11] Patent Number: 4,788,975
[45] Date of Patent: Dec. 6, 1988

[54] CONTROL SYSTEM AND METHOD FOR IMPROVED LASER ANGIOPLASTY

[75] Inventors: Leonid Shturman, Minnetonka; Steven L. Jensen, Coon Rapids, both of Minn.

[73] Assignee: Medilase, Inc., Minneapolis, Minn.

[21] Appl. No.: 117,666

[22] Filed: Nov. 5, 1987

[51] Int. Cl.$^4$ ............................................. A61B 17/36
[52] U.S. Cl. ............................... 128/303.1; 211/121.61
[58] Field of Search ................. 128/6, 303.1, 395–398, 128/419 P, 419 R; 219/121.61, 121.62

[56] References Cited

U.S. PATENT DOCUMENTS

| | | | |
|---|---|---|---|
| 4,418,688 | 12/1983 | Loeb | 128/6 |
| 4,448,188 | 5/1984 | Loeb | 128/6 |
| 4,538,613 | 9/1985 | Rosenberg | 128/395 |
| 4,576,177 | 3/1986 | Webster | 128/303.1 |
| 4,587,972 | 5/1986 | Morantte | 128/303.1 |
| 4,641,650 | 2/1987 | Mok | 128/303.1 |
| 4,641,912 | 2/1987 | Goldenberg | 128/6 |
| 4,648,892 | 3/1987 | Kittrell et al. | 128/303.1 |
| 4,654,024 | 3/1987 | Critteren et al. | 604/49 |
| 4,669,467 | 6/1987 | Willett et al. | 128/303.1 |
| 4,672,963 | 1/1987 | Barkey | 128/303.1 |
| 4,682,594 | 7/1987 | Mok | 128/303.1 |
| 4,706,656 | 11/1987 | Kuboto | 128/6 |
| 4,718,417 | 1/1988 | Kittrell et al. | 128/303.1 |
| 4,719,912 | 1/1988 | Weinberg | 128/303.1 |

FOREIGN PATENT DOCUMENTS 8606642 11/1986 World Int. Prop. O. .

OTHER PUBLICATIONS

*Continuous On–Line Assessment of Coronary Angioplasty with a Doppler Tipped Balloon Dilation Catheter* by Sibley, Bulle, Baxley, Dean and Whitlow, 1986.

*Fiberoptic Laser–Induced Fluorescence Detection of Atherosclertosis and Plaque Ablation; Potential for Laser Angioplasty Guidance,* by Deckelbaum, Stetz, Lam, Clubb, Cutruzola, Cabin and Long, 1986.

*Detection of Atherosclerotic Plaque and Characterization or Arterial Wall Structure by Laser Induced Florescence* by Sartori, Bossaler, Weilbacher, Henry and Roberts, 1986.

*Laser Induced Plaque Artherolysis with Tetracycline* by Abela, Barbieu, Roxey and Conti., 1986.

*Primary Examiner*—Max Hindenburg
*Attorney, Agent, or Firm*—Vidas & Arrett

[57] ABSTRACT

A control system and method for laser angioplasty or laser ablation or welding of tissue in general, in which firing of a laser catheter is correlated with movement of a vessel or other body chamber carrying the laser catheter, whereby the laser is fired only during those times its fiberoptic-delivered beam is aimed at plaque or other target in the vessel or chamber.

28 Claims, 2 Drawing Sheets

CONTROL SYSTEM AND METHOD FOR IMPROVED LASER ANGIOPLASTY

BACKGROUND OF THE INVENTION

The invention relates specifically to laser angioplasty and to improved methods and apparatus therefor. With this in mind, the invention will be specifically described with reference to laser systems and methods for ablating plaque, although it has broader applicability. For example, it is applicable to the so called hot probe laser approach as described in U.S. Pat. No. 4,650,024, entitled "Thermorecanalization Catheter and Method for Use", issued March 31, 1987. In its broader sense the invention relates to any medical treatment systems and method for effecting treatment to selected sites in the body in which cyclic or repetitive movement is involved.

The aiming of laser energy accurately at atherosclerotic plaque within a vessel, such as a coronary artery, is negatively affected by the continuous movement of the vessel. This movement is associated with cardiac contractions, hence relates to phases of the cardiac cycle. As a result of such movement a laser catheter positioned within a vessel also undergoes relative movement and may at times be aimed at plaque and at other times aimed at normal vessel wall.

Mechanical damage to vessels, including wall perforation, continues to be a major problem with laser angioplasty. The aiming of laser energy (delivered via a fiberoptic delivery system) is a major task. The continuous motion of the vessel wall significantly complicates aiming and delivering of laser energy accurately to the atherosclerotic plaque. The prior art has treated the movement of coronary arteries and other vessels as a problem rather than attempting to take advantage of the repetitive nature of the movement of coronary arteries as displayed from one cardiac cycle to another.

The present invention relates to a control system for timing the delivery of laser energy such that it accurately impinges on plaque or other intended target area.

SUMMARY OF THE INVENTION

According to this invention the repetitive motion of the walls of the ventricles (or heart chambers in general) and the motion of associated vessels during heart cycles is taken advantage of and delivery of laser energy for ablation of the plaque (or other type of obstruction or target) is provided only during specific, predetermined times or time intervals during a cardiac cycle or cycles. Thus, in accordance with this invention one takes into account the repetitive nature of the movement of the vessel carrying the laser catheter and uses the repetitive nature of the movement for timing the firing of the laser only when the laser beam (delivered via fiberoptic-based catheter) and the plaque or other obstruction or target are coincident i.e., at times when accurate aiming exists.

In accomplishing this it is necessary to identify, during a number of consecutive cardiac cycles, those times during the cycle when the laser catheter is aimed at the target area and not at normal vessel wall. It can be seen that during certain times of such a cycle repetitive movement of the vessel will bring the atherosclerotic lesion i.e., a target area into a position where the laser energy will impinge on it. Therefore, the laser energy delivery during such time or time intervals will be safer and will significantly diminish probability of vessel wall perforation. Consequently, the movement of the vessel is no longer treated as a problem but rather the motion is taken advantage of by timing its cyclic movement and selecting or defining those times or time intervals when the laser energy is coincident with respect to the targeted area, for firing the laser.

More specifically, with the proposed invention, after initially positioning and aiming the distal end of fiberoptic-based laser catheter at a target area such as plaque or some other obstruction or target area within the vessel, the entire cardiac cycle is artificially divided into a number of fixed time intervals, as determined by the physician-operator. For the purpose of establishing a cardiac cycle, the QRS complex from an electrocardiogram may be used to establish the beginning and end points of a repetitive cycle to be used. During a plurality of times within such a cycle an image or signal indicative of the position of the distal end of a laser catheter, relative to the target, may be obtained during each of those times. Such an image or signal (more than one may be involved and used) are stored, preferably in an electronic storage media such as a digital memory or video tape, for later review and use.

Images may include fluoroscopic or angiographic (both radiographic) images and or images from a fiberoptic angioscope. Signals may be also obtained from an ultrasound transducer mounted at the distal tip of a laser catheter. Also, laser induced fluorescence signals (plaque and normal vessel walls fluoresce differently in response to a laser radiation) may be used alone or simultaneously with other signals and/or images throughout any predetermined number of cardiac cycles.

All such data may be stored electronically for subsequent review by a physician-operator of the system. After sufficient data has been accumulated in the storage medium the images and signals may be reviewed frame by frame. It is preferable to review at the same time all images and signals which were obtained at the same time in the cycle. Window type presentation of multiple images and signals on one screen is also preferable. The review is not done in real time but at a speed convenient for the physician-operator. The review of the collected data allows the physician-operator to determine those times of the cycle during which the laser catheter is accurately aimed at the target area. Through the use of a microcomputer or other computer means, appropriate programming may then be placed into operation to control the firing of the laser catheter for delivery of laser radiation during upcoming cardiac cycles and only during those times or time intervals when it has been determined that the laser beam is aimed directly at or coincident with the target area.

In a simple system only one image or signal may be utilized to verify aiming. However, in a more sophisticated system, wherein one or more images and/or signals are stored for review, all of the images and signals which have been obtained simultaneously from several sources during given times of a cycle may be used to confirm the accurate or inaccurate aiming of the laser catheter at the target area.

Agreement concerning aiming between different sources of data confirms for the physician-operator those time intervals of the cycle when it is safe to activate the laser for ablating the target area. Trains of ablative laser pulses throughout these safe times or time intervals, which may be one time or time interval of one cycle or several cycles or several times or time intervals extending over a number of cycles may be utilized. Such a system of aiming verification will provide improved operation of a laser angioplasty system and is most preferred.

As indicated above, the QRS complex of an ECG may be used for establishing a cycle representative of the vessel movement and is preferred. However, other sources for establishing representative cycles may be used such as the blood pressure in the aorta, blood flow in the cardiac ventricle or aorta or an artificial pacing cycle may be established with the pacing pulse used as a reference.

DESCRIPTION OF THE DRAWING

The present invention will be apparent from the detailed description provided herein taken in conjunction with the accompanying drawing in which.

DETAILED DESCRIPTION OF PREFERRED EMBODIMENTS

In its preferred form, this invention will be practiced in combination with the laser catheter described in copending application Ser. No. 066,937, entitled Laser Angioplasty and filed June 25, 1987. That application is assigned to the same assignee as in this application. Its contents are incorporated herein by reference. The following description of the subject invention refers particularly to an overall system and method and not to any particular catheter construction.

Figure 1:
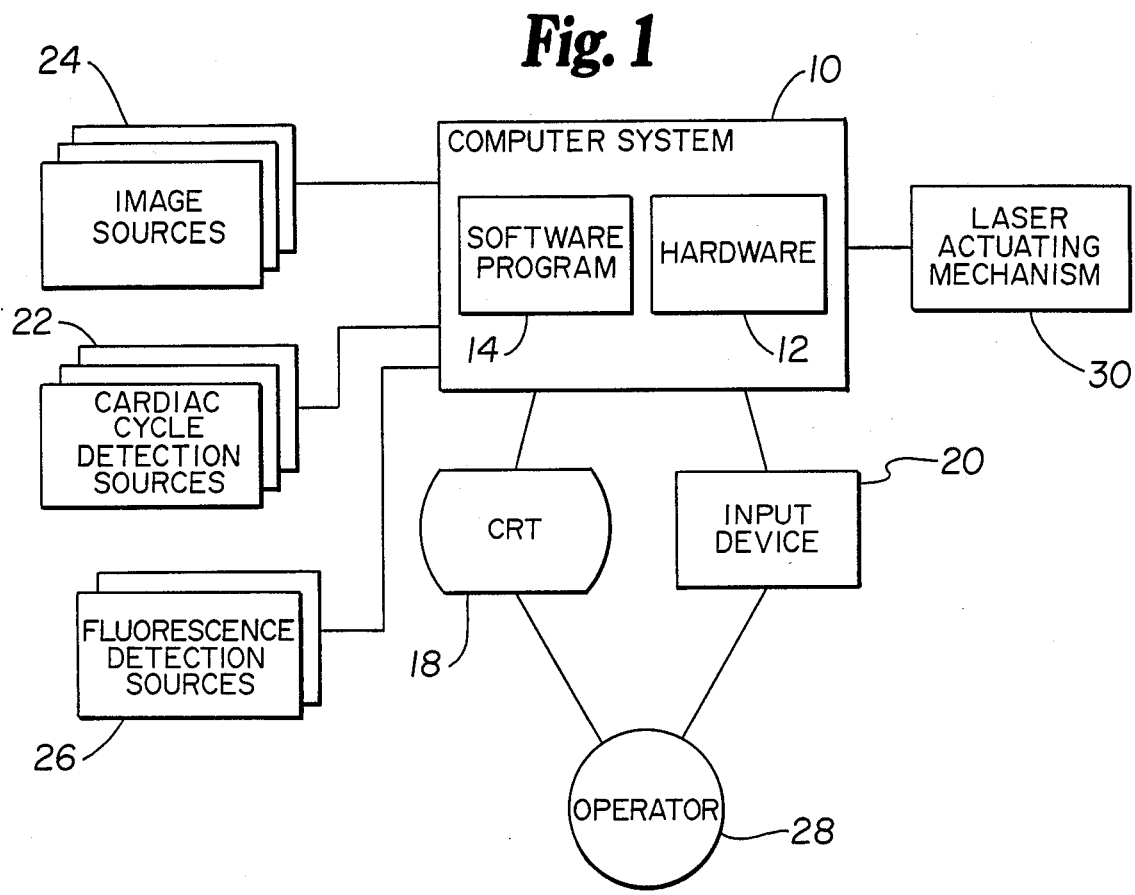
FIG. 1 is a block diagram, showing the construction of a hardware embodiment of the invention.

FIG. 1 shows an embodiment of the invention. In the Figure a computer system 10 includes computer hardware 12 and software program means 14. Hardware 12 includes storage means (not shown). Also connected to computer 10 are a display CRT 18 and a user input device such as a keyboard, mouse, light pen or joy stick arrangement or others 20. The storage means is constructed and arranged such that signals, such as electrocardiogram data including QRS complex time points or other cardiac cycle time points, may be used to trigger acquisition and/or storage of images and other data concerning the relative positions of the laser catheter and a target area in a vessel or chamber carrying the laser catheter. The images and other data may be generated by one or more various means 24 and 26 and are introduced into the storage means hardware.

Storage and digital image subsequent processing may be accomplished by a system such as the Trapix 5500 digital image processor available from Recognition Concepts Inc., 341 Skiway, P.O. Box 8510, Incline Village, Nev., 89450. Another imaging system known as View 2000 is available from a company known as Virtual Imaging, 725 Kieffer Rd., Sunnyvale, Calif. 94086.

The various positional data means indicated at 24 and 26 may take various forms. For example, one of these may take the form of an imaging system in which an image showing the relative positions of the laser catheter and the target area may be generated angiographically, including utilization of Digital subtraction Angioplasty (DSA) if necessary, or angioscopically and stored in the storage means for display on CRT 18. From such images one can determine if the laser catheter is accurately aimed at selected target area.

In addition to or in lieu of actual images, various sensing arrangements which generate a signal indicative of a positional relationship of the laser vis-a-vis the target area may also be used with the present invention. As already indicated, the fluorescence effect exhibited by plaque is different than the fluorescence effect exhibited by a vessel wall, the florescence being in response to impinging low level radiation. See the abstract of a presentation entitled *Fiberoptic Laser-Induced Fluorescence Detection of Atherosclerosis and Plaque Ablation; Potential for Laser Angioplasty Guidance*. by Decklebaum, Stetz, Lam, Clubb, Cutruzzola, Cabin and Long given at the American Heart Association in Dallas, Tex. and abstracted as paper #27 (II-7) in the Part 2, Volume 74, Number 4, October 1986, Manograph Number 124, Circulation Supplements, Abstracts from the 59th Scientific Sessons, American Heart Association. Also from the same sessions, see Abstract #25 (II-7) entitled *"Detection of Atherosclerotic Places and Characterization or Arterial wall Structure by Laser Induced Fluorescence"* by Sartori; Bossaler, Weilbacher, Henry and Roberts and see Abstract #26 (II-7) entitled *"Laser Induced Placue Atherolvsis with Tetracycline"* by Abela, Barbieu, Roxey and Conti. In accordance with this invention a sensing means responsive to such flourescence may be included in the system, the particular type of the fluorescence being indicative of when the catheter is on target and when it is not.

Likewise, a data signal may be generated by means of an ultrasound tranducer which may be mounted on the distal end of the laser catheter. See the abstract of a presentation entitled *"Continuous On-Line Assessment of Coronary Angioplasty with a Doppler Tipped Balloon Dilatation Catheter"* by Sibley, Bulle, Baxley, Dean and Whitlow given at the same Scientific Sessions above-identified and abstracted as #1828 (II-459). Such data may also be stored for later review and use. Ultrasound image or images can be reconstructed from such signals or data.

Figure 2:
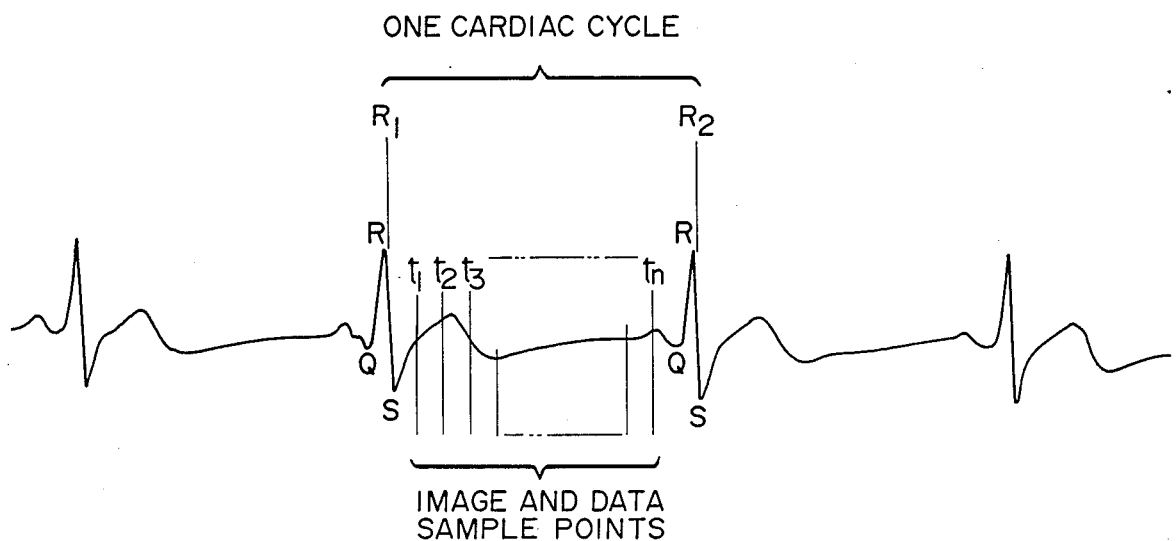
FIG. 2 is a representation of an electrocardiogram showing deflections resulting from atrial and ventricular electrical activity. The QRS complex is due to excitation of the ventricle and is used according to the invention to establish a repeatable time cycle.

With constructions such as those described above, after initially positioning a laser catheter in a vessel and aiming it at a target area, positional images and data and/or signals as described above generated by various modalities are obtained at predetermined times throughout any desired number of cardiac cycles. Such a cardiac cycle is shown in the electrocardiogram of FIG. 2 wherein the repeating cycle is defined by time between QRS complex $R_1$-$R_2$ of an ECG. In the cycle illustrated, a plurality of time points $t_1 \ldots t_n$ represent the times during which the images and/or signals are generated to determine whether the laser catheter is accurately aimed at the target area or not. Simultaneous collection of various positional images, data and/or signal by various modalities (whether carried by the catheter or independently operative means) such as 24 and 26 may be taken at each point of time $t_1 \ldots t_n$ for storage (on electronic memory means such as video tape or optical disc, etc.). Then, all of these images and data may be recalled and reviewed frame by frame preferably with simultanteous review of images and data from different imaging and data or signal sources obtained at the same time in the cardiac cycle.

This review is not done in real time but at a speed convenient for the physician-operator 28. Any number of cardiac cycles and number of times or time points per cycle may be selected by the physician-operator. The review of this data allows the physician-operator to determine those time or time intervals of the cycle during which the laser catheter is reliably and consistently aimed at the target area.

Then and only then, computerized control of the laser actuating mechanism 30 may be set through input device 20 to energize or trigger the laser or allow the laser beam to enter the shooting optical fiber of the laser catheter during those times or time intervals of the upcoming cycle when the catheter is reliably aimed at the target area.

If any abnormal pattern of cardiac activity is observed by the physician-operator or identified by computerized control system, the operator or the computerized control system is arranged to automatically block delivery of ablating laser radiation.

Figure 3:
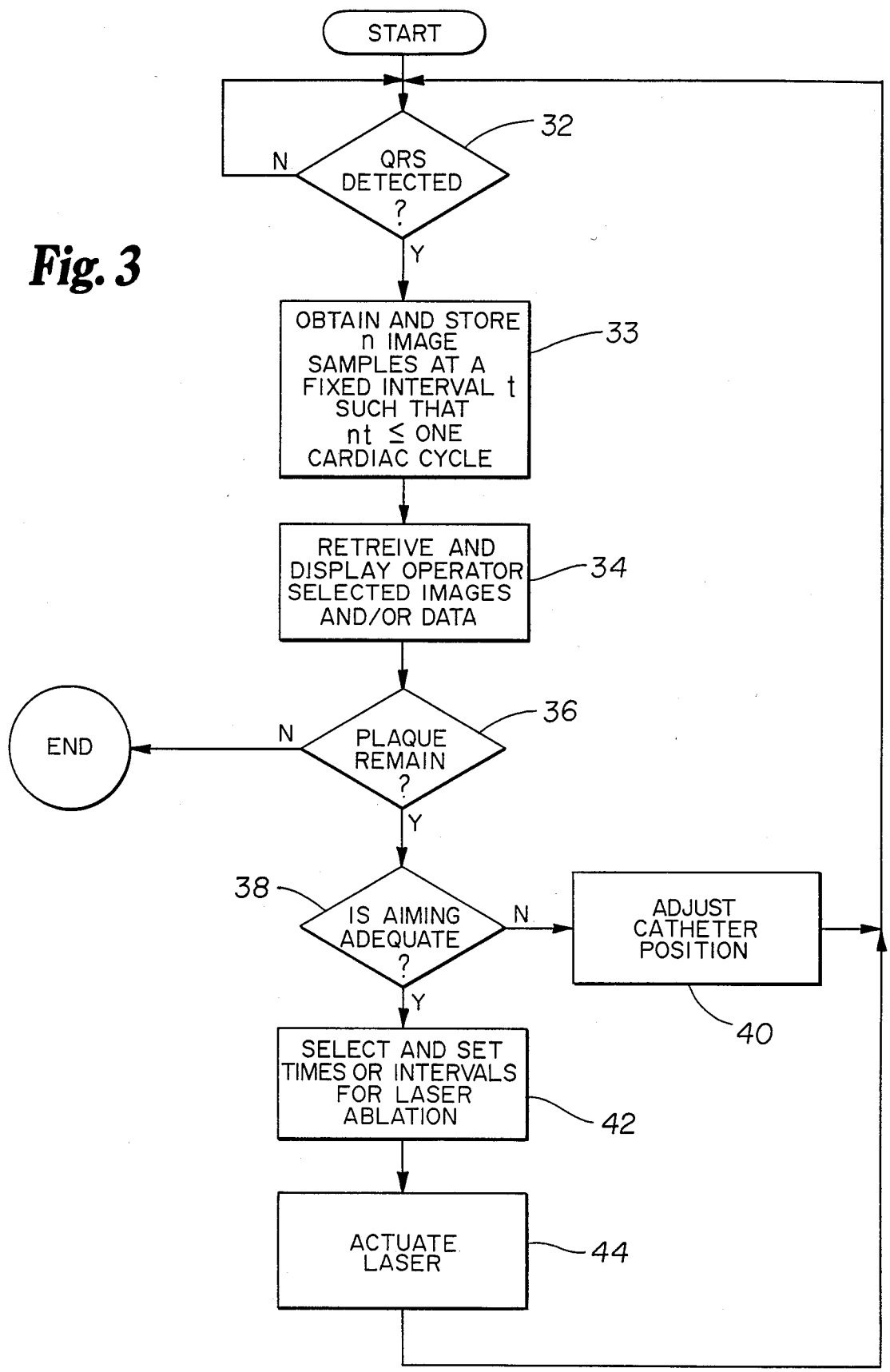
FIG. 3 is a flowchart showing the operation of the overall system.

FIG. 3 shows a program flow chart for the operations performed by the hardware shown in FIG. 1. FIG. 3 represents the various steps involved in selecting times during which to actuate the laser or otherwise allow laser radiation to impinge on a target area. The first step in this process occurs at 32 when the QRS time points are generated. 32 represents the step in which the time period cycle between two consecutive QRS complex points $R_1$-$R_2$ are determined. The next step is indicated at 33 in which the time period $R_1$-$R_2$ is divided into a number of times t and n number of images or data signals are obtained and stored from one or more instruments which the physician-operator selects for each of the time intervals $t_1$ to $t_n$ during one cycle. During next step 34, the images or data readings obtained in step 33 are displayed on the CRT in operator selected format. Step 36 indicates the point at which it is determined if plaque or other suitable target is present. Step 38 indicates a decision point in which the operator must decide whether the laser is accurately aimed during one or more of the times or time intervals. If the laser is not aimed at the plaque during one or more of the time intervals, step 40 is executed, which involves adjusting the catheter position and returning steps 32-38. If the operator determines that the laser is aimed at plaque or the like during one or more time intervals, step 42 is performed. Step 42 consists of the operator selecting the particular time or time interval during which to fire the laser in an upcoming cycle or cycles and inputting this time or time intervals and the number of cycles into the computer. The last step indicated at 44 is triggering the laser actuation mechanism which either activates the laser itself or allows the laser beam to enter the laser catheter.

From the foregoing description it will be seen in accordance with this invention that the safe firing of a laser catheter in an angioplasty system may be accomplished. Preferably this is done by using various modalities associated with the catheter and independent of it to generate positional data and confirm the adequacy of the aiming or the need to adjust same.

What is claimed is:

1. In combination with a laser angioplasty system in which a laser catheter is positioned within a moving vessel and oriented to impinge radiation upon a selected target site within the vessel, the improvement comprising:

means for defining a cycle representative of repetitive vessel movement;

means for defining the position of the laser catheter relative to the selected target site during various times of the cycle, and means for activating the laser catheter at a selected time or times to impinge laser radiation on the target site during an upcoming cycle or cycles.

2. The combination of Claim 1 in which the means for defining a cycle representative of vessel movement defines an aspect of the cardiac cycle.

3. The combination of claim 1 in which the vessel is a coronary artery and the means for defining a cycle representative of vessel movement defines an characteristic relative to the coronary artery.

4. The combination of claim 1 wherein the means for defining the cycle includes electrocardiographic data.

5. The combination of claim 4 wherein the cycle is defined by the QRS complex.

6. The combination of claim 1 wherein the means for defining the position of the laser catheter includes at least one imaging system.

7. In combination with a laser angioplasty system for the delivery of laser energy to atherosclerotic plaque in a vessel and for ablation of the plaque therein, the combination comprising:

a laser catheter including an actuating mechanism therefore;

first means responsive to an aspect representative of repetitive vessel movements for defining a time period cycle representative thereof and for dividing the time period cycle into a variable number of fixed times or time intervals;

second means responsive to the relative positions of the laser catheter and the plaque in the vessel for identifying those times or time intervals during a cycle (or a cardiac cycle) when the laser catheter is aimed at the plaque and those times or time intervals when it is not, and computer means responsive to said first means and said second means for controlling the actuation of the laser catheter during at least one time or time interval of an upcoming cardiac cycle in which the laser catheter is oriented to the plaque.

8. The combination of Claim 7 in which the aspect representative of repetitive vessel movement relates to the cardiac cycle.

9. The combination of claim 7 wherein the first means includes electrocardiographic data and further includes associated means for defining a time period represented by the electrocardiogram QRS complex generated thereby and for defining a plurality of times therebetween.

10. The combination of claim 7 wherein the second means includes image acquisition and processing means for visually displaying on a CRT images of the vessel toward which the catheter is oriented and orientation of the catheter or its aiming mechanism relative to a target area.

11. The combination of claim 10 wherein the second means includes angiography imaging means.

12. The combination of claim 10 wherein the second means includes angioscopic imaging means.

13. The combination of claim 7 wherein the second means includes signal generating means and sensing means for sensing when the catheter is oriented toward the plaque in the vessel.

14. The combination of claim 13 wherein the second means includes a laser induced fluorescent signal.

15. The combination of claim 13 wherein the second means includes ultrasound signal means.

16. The combination of claim 7 wherein the first and second means generate electrical output signals representative of time and positional data, respectively.

17. The combination of claim 16 wherein the computer means is electronically connected to the first and second means and includes electronic data storage and display means for storing and displaying the time and positional data at operator command.

18. The combination of claim 17 wherein the computer means further includes manual data entry means for selecting certain times or time intervals during which the catheter is oriented toward plaque in the vessel.

19. The combination of claim 18 further including means for automatically triggering the firing of the laser catheter during the selected time intervals during an upcoming cycle or cycles.

20. The combination of claim 18 including means for deactivating the laser catheter.

21. In combination with a medical treatment device in which a treatment means is positioned within a moving body and oriented toward a selected site therewithin for effecting treatment thereof, the improvement comprising:
means for defining a repetitive time cycle representative of body movement;
means for defining the position of the treatment means relative to the selected site during various times of the time cycle, and
means for activating the treatment means at a selected time or times to effect treatment of the selected site.

22. In combination with a medical treatment system for effecting treatment to a selected site in a body or body part, the combination comprising:
medical treatment means inserting into the body including an actuating mechanism therefore;
first means responsive to repetition body movements for defining a time period representative thereof and for dividing the time period into a variable number of fixed times;
second means responsive to the relative positions of the medical treatment means and the site in the body for identifying those times or time intervals during a time period when the treatment means is oriented toward the site and those times or time intervals when it is not, and
computer means responsive to said first means and said second means for controlling the actuation of the medical treatment means during at least one time or time interval of a cycle in which it is oriented toward selected site during upcoming cycle.

23. A method of timing the actuation of a laser angioplasty catheter carried in a moving vessel to assure impingement of laser radiation upon atherosclerotic plaque rather than on the vessel wall, the method comprising:
inserting the catheter into a vessel and positioning it toward a target area therein;
establishing a repeating time cycle based on vessel movement, including discrete times within the cycle;
selecting those discrete times in the cycle during which the catheter aiming mechanism is aimed at the plaque, and
arranging for the actuation of the laser during at least one of those determined discrete times in an upcoming cycle.

24. The method of claim 23 in which the step of selecting those times when aiming is at the plaque includes the use of an image acquisition, storage and display systems.

25. The method of claim 23 in which the step of selecting those times when aiming is at the plaque includes the use of sensing means for providing data that indicates the orientation of the catheter relative to the plaque.

26. The method of claim 23 in which the step of arranging for actuation of the catheter includes the use of computer means for correlating the selecting step with the actuation of the laser.

27. The method of claim 23 wherein the selecting step includes data from a plurality of modalities, some associated with the catheter per se and some independent thereof.

28. A method of timing the actuation of a medical treatment system in which a medical treatment means is inserted into the body and to assure effecting treatment by the means to a selected site in the body, the method comprising:
inserting the medical treatment means into the body and positioning it toward a selected site therein;
establishing a repeating time cycle based on certain body movement, including discrete times within the cycle;
selecting those discrete times in the cycle during which the medical treatment means is oriented toward the site and
arranging for the actuation of the medical treatment means during at least one of those determined discrete times or time intervals during an upcoming cycle.

* * * * *

UNITED STATES PATENT AND TRADEMARK OFFICE
CERTIFICATE OF CORRECTION

PATENT NO. : 4,788,975
DATED : December 6, 1988
INVENTOR(S) : Leonid Shturman

It is certified that error appears in the above-identified patent and that said Letters Patent is hereby corrected as shown below:

Col. 1, line 12, delete "4,650,024" and insert "4,654,024"

Col. 3, line 34, delete "in" and insert - "is"

Col. 4, line 18, delete "Manograph" and insert "Monograph"

Col. 4, line 20, delete "Sessons" and insert "Sessions"

Signed and Sealed this

Thirtieth Day of May, 1989

Attest:

DONALD J. QUIGG

Attesting Officer

Commissioner of Patents and Trademarks

US004788975B1

REEXAMINATION CERTIFICATE (3742nd)

United States Patent [19]
Shturman et al.

[11] B1 4,788,975
[45] Certificate Issued Mar. 2, 1999

[54] CONTROL SYSTEM AND METHOD FOR IMPROVED LASER ANGIOPLASTY

[75] Inventors: Leonid Shturman, Minnetonka; Steven L. Jensen, Coon Rapids, both of Minn.

[73] Assignee: Trimedyne, Inc., Irvine, Calif.

Reexamination Request:
No. 90/004,942, Feb. 19, 1998

Reexamination Certificate for:
Patent No.: 4,788,975
Issued: Dec. 6, 1988
Appl. No.: 117,666
Filed: Nov. 5, 1987

Certificate of Correction issued May 13, 1989.

[51] Int. Cl.$^6$ ................................................ A61B 17/36
[52] U.S. Cl. ................................................ 606/7; 606/12
[58] Field of Search ............ 606/2, 7–15; 600/519–522, 600/527

[56] References Cited

PUBLICATIONS

Cornelis J. Slager et al., *Vaporization of Atherosclerotic Plaques by Spark Erosion*, J. Am. Coll. Cardiol., vol. 5, No. 6, Jun. 1985:1382–1386.

George S. Abela et al., *Laser Angioplasty with Angioscopic Guidance in Humans*, J. Am. Coll. Cardiol., vol. 8, No. 1, Jul. 1986:184–192.

*Primary Examiner*—Max Hindenburg

[57] ABSTRACT

A control system and method for laser angioplasty or laser ablation or welding of tissue in general, in which firing of a laser catheter is correlated with movement of a vessel or other body chamber carrying the laser catheter, whereby the laser is fired only during those times its fiberoptic-delivered beam is aimed at plaque or other target in the vessel or chamber.

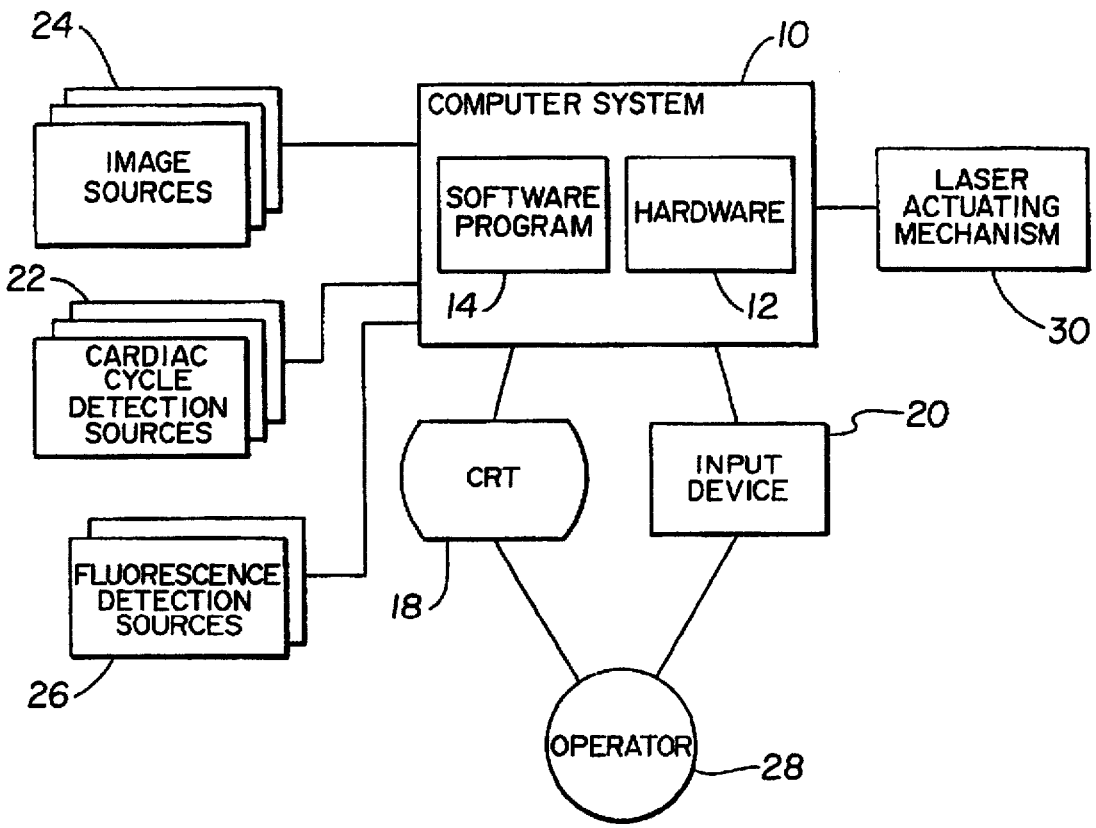

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim(s) 1-28 is confirmed.

1. In combination with a laser angioplasty system in which a laser catheter is positioned within a moving vessel and oriented to impinge radiation upon a selected target site within the vessel, the improvement compris- ing:

means for defining a cycle representative of repetitive vessel movement;

means for defining the position of the laser catheter relative to the selected target site during various times of the cycle, and means for activating the laser catheter at a selected time or times to impinge laser radiation on the target site during an upcoming cycle or cycles.

* * * * *